US010195126B2

(12) United States Patent
Nicou et al.

(10) Patent No.: US 10,195,126 B2
(45) Date of Patent: *Feb. 5, 2019

(54) DYE COMPOSITION COMPRISING A PARA-PHENYLENEDIAMINE OXIDATION BASE AND A HETEROCYCLIC OXIDATION BASE

(71) Applicant: L'OREAL, Paris (FR)

(72) Inventors: Valerie Nicou, Clichy (FR); Isabelle Rollat, Paris (FR); Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,060

(22) PCT Filed: Dec. 17, 2015

(86) PCT No.: PCT/EP2015/080373
§ 371 (c)(1),
(2) Date: Jun. 16, 2017

(87) PCT Pub. No.: WO2016/097229
PCT Pub. Date: Jun. 23, 2016

(65) Prior Publication Data
US 2017/0354580 A1    Dec. 14, 2017

(30) Foreign Application Priority Data
Dec. 17, 2014    (FR) ..................... 14 62624

(51) Int. Cl.
*A61Q 5/10*    (2006.01)
*A61K 8/41*    (2006.01)
*A61K 8/49*    (2006.01)

(52) U.S. Cl.
CPC .............. *A61K 8/411* (2013.01); *A61K 8/494* (2013.01); *A61Q 5/10* (2013.01); *A61K 2800/882* (2013.01)

(58) Field of Classification Search
CPC .......... A61Q 5/10; A61K 8/494; A61K 8/411; A61K 2800/882
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 3,206,462 A | 9/1965 | McCarty |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,075,136 A | 2/1978 | Schaper |
| 4,131,576 A | 12/1978 | Iovine et al. |
| 4,165,367 A | 8/1979 | Chakrabarti |
| 4,166,894 A | 9/1979 | Schaper |
| RE30,199 E | 1/1980 | Rose et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,608,250 A | 8/1986 | Jacquet et al. |
| 4,719,099 A | 1/1988 | Grollier et al. |
| 4,839,166 A | 6/1989 | Grollier et al. |
| 4,840,639 A | 6/1989 | Husemeyer et al. |
| 4,996,059 A | 2/1991 | Grollier et al. |
| 5,009,880 A | 4/1991 | Grollier et al. |
| 5,061,289 A | 10/1991 | Clausen et al. |
| 5,089,252 A | 2/1992 | Grollier et al. |
| 5,380,340 A | 1/1995 | Neunhoeffer et al. |
| 5,457,200 A | 10/1995 | Zimmermann et al. |
| 5,534,267 A | 7/1996 | Neunhoeffer et al. |
| 5,616,150 A | 4/1997 | Moeller et al. |
| 5,663,366 A | 9/1997 | Neunhoeffer et al. |
| 5,766,576 A | 6/1998 | Lowe et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

STIC Search Report dated Sep. 21, 2017.*

(Continued)

*Primary Examiner* — Eisa B Elhilo
(74) *Attorney, Agent, or Firm* — The Marbury Law Group, PLLC

(57) ABSTRACT

The present invention relates to a composition for dyeing keratin fibres, in particular keratin fibres such as the hair, comprising: a) at least one oxidation base 3-(2,5-diaminophenyl)-1-propanol acid salts thereof or solvates thereof such as hydrates; b) at least one heterocyclic oxidation base; c) at least one coupler; d) optionally at least one fatty substance; e) optionally at least one basifying agent; and f) optionally at least one chemical oxidizing agent. The invention also relates to a process for dyeing keratin fibres such as the hair using the composition of the invention, and to a multi-compartment device for using the composition of the invention.

19 Claims, No Drawings

(56) References Cited

U.S. PATENT DOCUMENTS

| | | | |
|---|---|---|---|
| 5,928,385 A | 7/1999 | Cotteret et al. | |
| 5,958,392 A | 9/1999 | Grollier et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,342,079 B1 | 1/2002 | Pan et al. | |
| 6,503,282 B1 * | 1/2003 | Braun | A61K 8/411 564/443 |
| 6,645,258 B2 | 11/2003 | Vidal et al. | |
| 6,730,789 B1 | 5/2004 | Birault et al. | |
| 3,066,781 A1 | 11/2011 | Hercouet et al. | |
| 2002/0010970 A1 | 1/2002 | Cottard et al. | |
| 2002/0046431 A1 | 4/2002 | Laurent et al. | |
| 2010/0154136 A1 | 6/2010 | Hercouet et al. | |
| 2011/0158925 A1 | 6/2011 | Ascione et al. | |
| 2013/0048007 A1 | 2/2013 | Fadli | |
| 2014/0137342 A1 | 5/2014 | Guerin et al. | |
| 2014/0318566 A1 * | 10/2014 | Mignon | A61K 8/31 132/221 |
| 2015/0082554 A1 | 3/2015 | Allard et al. | |
| 2015/0202142 A1 | 7/2015 | Charrier et al. | |
| 2015/0335563 A1 | 11/2015 | Allard et al. | |

FOREIGN PATENT DOCUMENTS

| | | |
|---|---|---|
| DE | 4133957 A1 | 4/1993 |
| DE | 19543988 A1 | 5/1997 |
| EP | 0007537 A1 | 2/1980 |
| EP | 0080976 A1 | 6/1983 |
| EP | 0122324 A1 | 10/1984 |
| EP | 0337354 A1 | 10/1989 |
| EP | 0770375 A1 | 5/1997 |
| EP | 1166749 A2 | 1/2002 |
| EP | 2198929 A1 | 6/2010 |
| EP | 2338463 A1 | 6/2011 |
| FR | 1400366 A | 5/1965 |
| FR | 2077143 A5 | 10/1971 |
| FR | 2080759 A1 | 11/1971 |
| FR | 2190406 A2 | 2/1974 |
| FR | 2270846 A1 | 12/1975 |
| FR | 2316271 A1 | 1/1977 |
| FR | 2320330 A1 | 3/1977 |
| FR | 2336434 A1 | 7/1977 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2519863 A1 | 7/1983 |
| FR | 2598611 A1 | 11/1987 |
| FR | 2733749 A1 | 11/1996 |
| FR | 2801308 A1 | 5/2001 |
| FR | 2886136 A1 | 12/2006 |
| FR | 2988591 A1 | 10/2013 |
| FR | 2988594 A1 | 10/2013 |
| FR | 2988595 A1 | 10/2013 |
| FR | 2988598 A1 | 10/2013 |
| FR | 2994085 A1 | 2/2014 |
| GB | 1021400 A | 3/1966 |
| GB | 1026978 A | 4/1966 |
| GB | 1153196 A | 5/1969 |
| GB | 1546809 A | 5/1979 |
| JP | 02-019576 A | 1/1990 |
| JP | 05-163124 A | 6/1993 |
| WO | 80/00214 A1 | 2/1980 |
| WO | 94/08969 A1 | 4/1994 |
| WO | 94/08970 A1 | 4/1994 |
| WO | 94/24988 A1 | 11/1994 |
| WO | 96/15765 A1 | 5/1996 |
| WO | WO 2012/080321 A2 * | 4/1997 |
| WO | 01/51019 A1 | 7/2001 |
| WO | 2012/080321 A2 | 6/2012 |
| WO | 2012080288 A1 | 6/2012 |
| WO | 2012080289 A2 | 6/2012 |
| WO | 2013/144260 A2 | 10/2013 |
| WO | 2013/152956 A2 | 10/2013 |
| WO | 2014/020148 A1 | 2/2014 |
| WO | WO2014/020148 A1 * | 2/2014 |
| WO | 2016/096654 A1 | 6/2016 |
| WO | 2016/096655 A1 | 6/2016 |
| WO | 2016/097022 A1 | 6/2016 |
| WO | 2016/097226 A1 | 6/2016 |
| WO | 2016/097227 A1 | 6/2016 |
| WO | 2016/097228 A1 | 6/2016 |

OTHER PUBLICATIONS

International Search Report for PCT/EP2015/079434, dated Feb. 1, 2016.
International Search Report for PCT/EP2015/080051, dated Mar. 9, 2016.
International Search Report for PCT/EP2015/079432, dated Mar. 16, 2016.
International Search Report for PCT/EP2015/080370, dated Mar. 14, 2016.
International Search Report for PCT/EP2015/080371, dated Mar. 24, 2016.
International Search Report for PCT/EP2015/080372, dated May 3, 2016.
International Search Report for PCT/EP2015/080373, dated Feb. 9, 2016.
Non-Final Office Action for co-pending U.S. Appl. No. 15/536,998, dated Sep. 29, 2017.
Non-Final Office Action for co-pending U.S. Appl. No. 15/537,029, dated Oct. 2, 2017.
Non-Final Office Action for co-pending U.S. Appl. No. 15/537,041, dated Oct. 2, 2017.
Final Office Action for copending U.S. Appl. No. 15/537,029, dated Apr. 17, 2018.
Final Office Action for copending U.S. Appl. No. 15/536,998, dated May 14, 2018.
Non-Final Office Action for copending U.S. Appl. No. 15/537,016, dated Jul. 10, 2018.
Non-Final Office Action for copending U.S. Appl. No. 15/537,225, dated Jul. 10, 2018.
Final Office Action for copending U.S. Appl. No. 15/537,041, dated May 18, 2018.
Notice of Allowance for copending U.S. Appl. No. 15/537,029, dated Aug. 1, 2018.

* cited by examiner

DYE COMPOSITION COMPRISING A PARA-PHENYLENEDIAMINE OXIDATION BASE AND A HETEROCYCLIC OXIDATION BASE

CROSS REFERENCE TO RELATED APPLICATIONS

This is a national stage application of PCT/EP2015/080373, filed internationally on Dec. 17, 2015, which claims priority to French Application No. 1462624, filed on Dec. 17, 2014, both of which are incorporated by reference herein in their entireties.

The present invention relates to a composition for dyeing keratin fibres using a specific para-phenylenediamine oxidation base and a heterocyclic oxidation base.

Many people have sought for a long time to modify the colour of their hair and in particular to hide their grey hair.

One of the dyeing methods is "permanent" or oxidation dyeing, which uses dye compositions containing oxidation dye precursors, generally known as oxidation bases. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouring modifiers, the latter being chosen especially from aromatic meta-diamines, meta-aminophenols, meta-diphenols and certain heterocyclic compounds such as indole compounds. The variety of the molecules used as oxidation bases and couplers allows a wide range of colours to be obtained.

Permanent dyeing processes thus consist in using, with the composition containing the dye precursors, an aqueous composition comprising at least one oxidizing agent, under alkaline pH conditions in the vast majority of cases. The role of this oxidizing agent is to at least partly degrade the melanin of the hair, which, depending on the nature of the oxidizing agent present, leads to more or less pronounced lightening of the fibres. The oxidizing agent used is generally hydrogen peroxide.

The basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

In the long term, the use of an oxidizing agent and an alkaline agent may lead to degradation of the keratin fibres and also to inconvenience at the time of use; in particular, ammonia may give rise to inconvenience to the user due to its strong characteristic odour.

Moreover, not only may the user be inconvenienced by the odour, but he may also be confronted with greater risks of intolerance, for instance irritation of the scalp, which is especially reflected by stinging.

It is also important to obtain intense colouring, which is resistant to external factors such as light, shampoos and sweat, and which is as uniform as possible along the entire fibre, irrespective of the level of damage of the keratin fibre.

Oxidation bases of the para-phenylenediamine type are commonly used in the field of hair dyeing. It is known in practice, for example, to use 3-(2,5-diaminophenyl)-1-propanol (or 2-y-hydroxypropyl-para-phenylenediamine) in oxidation dyeing, especially in document WO 80/00214. However, the dye compositions obtained using this oxidation base are not always satisfactory especially for ensuring suitable coverage of grey hair with an acceptable colouring selectivity between the root and the end and/or sufficient fastness with respect to external attacking factors such as light, shampoos, bad weather, etc.

One of the objects of the present invention is to propose compositions for dyeing human keratin fibres such as the hair, which have superior dyeing properties relative to the existing compositions.

In particular, the composition according to the invention in the presence of a chemical oxidizing agent must make it possible to obtain colours that are satisfactory, especially in terms of power, but also with sufficient uniformity of the colour from the end to the root of the hair, which makes it possible to avoid a "root" effect of the colouring. Finally, it is also possible to obtain colourings that are very stable towards external agents.

Furthermore, the invention makes it possible to achieve substantial degrees of lightening while at the same time colouring, and does so without using oxidizing agents such as persalts or increasing the amount of chemical oxidizing agent or of basifying agent.

Moreover, the composition of the invention makes it possible to obtain formulations that are less malodorous during their application to the hair or during their preparation.

These aims and others are achieved by the present invention, one subject of which is thus a composition for dyeing keratin fibres, in particular human keratin fibres such as the hair, comprising:
  a) at least one oxidation base 3-(2,5-diaminophenyl)-1-propanol and/or acid salts thereof and/or solvates thereof such as hydrates;
  b) at least one heterocyclic oxidation base as defined in claim 1;
  c) at least one coupler;
  d) optionally at least one fatty substance, which is preferably liquid and non-silicone-based;
  e) optionally at least one basifying agent; and
  f) optionally at least one chemical oxidizing agent.

A subject of the invention is also a process for dyeing keratin fibres such as the hair using the composition of the invention, and a multi-compartment device for using the composition of the invention.

Furthermore, the processes according to the invention use formulations that are less malodorous during their application to the hair or during their preparation.

Other characteristics and advantages of the invention will emerge more clearly on reading the description and the examples that follow.

In the text hereinbelow, and unless otherwise indicated, the limits of a range of values are included within that range. The expression "at least one" is equivalent to the expression "one or more".

d) Fatty Substances

As has already been mentioned, the composition of the invention may comprise one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of use in the invention do not contain any salified or unsalified carboxylic acid groups (—C(O)OH or —C(O)O⁻). The fatty substances of the invention are neither polyoxyalkylenated nor polyglycerolated.

Preferably, the fatty substances used in the composition according to the invention are non-silicone oils.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, pumpkin oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1, 3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, and linear or branched, and comprise from 6 to 30 carbon atoms and more particularly from 8 to 30 carbon atoms. Mention may be made, for example, of cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol.

The wax(es) that may be used in the composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this alternative form can also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose. An example that may be mentioned is the product sold under the name Glucate® DO by the company Amerchol, which is a methylglucose dioleate.

Examples of sugar esters or mixtures of sugar esters of fatty acids that may also be mentioned include:
 the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
 the products sold under the name Ryoto Sugar Esters, for example referenced B370 and corresponding to sucrose behenate formed from 20% monoester and 80% di-triester-polyester;
 the sucrose monopalmitostearate-dipalmitostearate sold by the company Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
 the Silbione® oils of the 47 and 70 047 series or the Mirasil® oils sold by Rhodia, for instance the oil 70 047 V 500 000;
 the oils of the Mirasil® series sold by the company Rhodia;
 the oils of the 200 series from the company Dow Corning, such as DC200 with—a viscosity of 60 000 mm$^2$/s;
 the Viscasil° oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The organomodified silicones that may be used in accordance with the invention are silicones as defined previously and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
 the Silbione® oils of the 70 641 series from Rhodia;
 oils of the Rhodorsil® 70 633 and 763 series from Rhodia;
 the oil Dow Corning 556 Cosmetic Grade Fluid from Dow Corning;
 the silicones of the PK series from Bayer, such as the product PK20;
 the silicones of the PN and PH series from Bayer, such as the products PN1000 and PH1000;
 certain oils of the SF series from General Electric, such as SF 1023, SF 1154, SF 1250 and SF 1265.

Among the organomodified silicones, mention may also be made of polyorganosiloxanes comprising:
 substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
 alkoxy groups such as the product sold under the name Silicone Copolymer F-755 by SWS Silicones, and Abil Wax® 2428, 2434 and 2440 by the company Goldschmidt.

Preferably, the fatty substances according to the invention are non-silicone.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof, which are preferably liquid.

Preferably, the fatty substance(s) are chosen from liquid petroleum jelly, polydecenes, liquid fatty alcohols, liquid esters of fatty acids and/or of fatty alcohols, or mixtures thereof.

Even more preferentially, the fatty substances are chosen from liquid petroleum jelly and octyldodecanol.

According to a particular embodiment, the composition contains at least one fatty substance. When they are present, the content of fatty substances is preferably at least 10% by weight relative to the total weight of the composition.

According to this particular embodiment, the composition according to the invention comprises at least 10% by weight of non-silicone fatty substances, in particular non-silicone oils, relative to the total weight of the composition of the invention. More particularly, the composition according to the invention comprises at least 25% by weight of fatty substances, which are preferably non-silicone, in particular non-silicone oils, relative to the total weight of the composition.

The composition according to the invention more particularly has a fatty substance content ranging from 15% to 80% by weight, preferably from 25% to 75% by weight, better still from 30% to 70% by weight and even more advantageously from 30% to 60% by weight relative to the weight of the composition.

According to a particular embodiment, when the composition contains the oxidizing agent and the basifying agent, then the composition according to the invention preferably contains more than 25% of fatty substances. According to this variant, the composition preferably contains more than 30% of fatty substances.

b) Heterocyclic Oxidation Bases

According to the invention, the term "heterocyclic base" means an oxidation base comprising a 5-, 6-, 7- or 8-membered aromatic or non-aromatic ring and from 1 to 3 heteroatoms chosen from nitrogen, sulfur and oxygen atoms. These heterocycles may be fused to other heterocycles or to a phenyl group. They may be substituted with a halogen atom; a $(C_1-C_4)$alkyl radical; a $(C_1-C_4)$alkoxy radical; a hydroxyl radical; an amino radical; a $(C_1-C_4)$alkylamino radical; di$(C_1-C_4)$alkylamino in which the two alkyl groups may, together with the nitrogen atom to which they are attached, form a ring that may be interrupted with one or more nitrogen, oxygen or sulfur atoms. These heterocycles may also be quaternized with a $(C_1-C_4)$alkyl radical. The alkyl or alkoxy radicals described above may optionally be substituted, preferably with one or more hydroxyl or amino groups.

The term "cationic heterocycle" means a heterocycle as described previously containing one or more cationic radicals of the quaternary ammonium type.

Examples of cationic radicals that may be mentioned include radicals of the type—$N^+R_{17}R_{18}R_{19}$, for example trimethylammonium, triethylammonium, dimethylethylammonium, diethylmethylammonium, diisopropylmethylammonium, diethylpropylammonium, β-hydroxyethyldiethylammonium, di(β-hydroxyethyl)-methylammonium and tri(β-hydroxyethyl)ammonium radicals. Examples of cationic heterocycles that may be mentioned include imidazolium, pyridinium, piperazinium, pyrrolidinium, morpholinium, pyrimidinium, thiazolium, benzimidazolium, benzothiazolium, oxazolium, benzotriazolium, pyrazolium, triazolium and benzoxazolium heterocycles.

As heterocyclic oxidation bases that are useful in the present invention, mention may be made of pyridines, pyrimidines, aminopyrazolones, aminopyrrolidines, aminopyrazolines and aminoindazoles, and derivatives thereof.

The heterocyclic bases are more particularly chosen from pyridine derivatives, pyrimidine derivatives and pyrazolone derivatives and the addition salts thereof or solvates thereof.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof or solvates thereof.

Other pyridine oxidation bases that are useful according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-[(3-aminopyrazolo[1,5-a]pyrid-2-yl)oxy]ethanol and also the addition salts thereof or solvates thereof.

Among the pyrimidine derivatives, mention may be made of the compounds described, for example, in patents DE 2359399, JP 88169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

According to a particularly preferred embodiment, the heterocyclic oxidation base(s) are chosen from the compounds of formula (I), the addition salts thereof and solvates thereof:

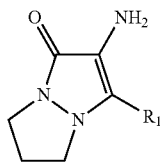

(I)

in which $R_1$ represents an amino group, a $C_1$ to $C_4$ alkyl group, optionally substituted with one or more hydroxyl or amino groups, a $C_1$ to $C_4$ alkoxy group, optionally substituted with one or more hydroxyl or amino groups.

(i) the compounds of formula (II) or (III), the addition salts thereof and solvates thereof:

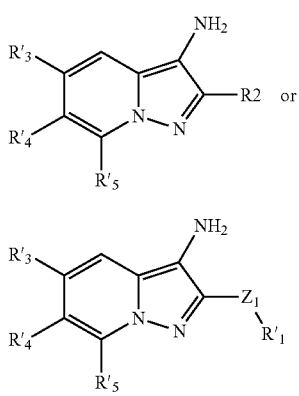

(II)

or (III)

in which $R_2$ represents an amino group, a $C_1$ to $C_4$ alkyl group, optionally substituted with one or more hydroxyl or amino groups, a $C_1$ to $C_4$ alkoxy group, optionally substituted with one or more hydroxyl or amino groups; and $Z_1$ represents a covalent bond, a radical —$NR'_6(CH_2)_q$— or a radical —$O(CH_2)_p$— with $R'_6$ representing a hydrogen atom, a $C_1$-$C_6$ alkyl radical optionally substituted with one or more hydroxyl groups, p denoting an integer ranging from 0 to 6, q denoting an integer ranging from 0 to 6 and $R'_1$ is a cationic radical; and the radicals $R'_3$, $R'_4$ and $R'_5$ may independently be a hydrogen atom or a $C_1$-$C_4$ alkyl radical which may be substituted. Examples that may be mentioned include methyl, ethyl, hydroxyethyl, aminoethyl, propyl and butyl radicals. According to a particular embodiment, $R'_3$, $R'_4$ and $R'_5$ independently represent a hydrogen atom or a $C_1$-$C_4$ alkyl radical.

$R'_4$ and $R'_5$ may together form a partially saturated or unsaturated 5- or 8-membered ring, especially an optionally substituted cyclopentene or cyclohexene.

As cationic groups, mention may be made for $R'_1$ of a cationic heterocycle or a heterocycle substituted with a cationic radical. Examples that may be mentioned include imidazoles substituted with a quaternary ammonium radical or imidazoliums, piperazines substituted with a quaternary ammonium radical or piperaziniums, pyrrolidines substituted with a quaternary ammonium radical or pyrrolidiniums, and diazepanes substituted with a quaternary ammonium radical or diazepaniums. $R'_1$ may also be chosen from trialkylammonium, tri(hydroxyalkyl)ammonium, hydroxyalkyl-dialkyl-ammonium and di(hydroxyalkyl)alkylammonium cationic radicals.

Preferably, in the compounds of formula (I), $R_1$ represents an amino group.

Preferably, in the compounds of formula (II), $R_2$ represents a $C_1$ to $O_4$ alkoxy group, optionally substituted with one or more hydroxyl groups, and preferentially represents a hydroxyethoxy group.

Among the compounds of formula (I) it will be preferred to use 2,3-diamino-6,7-dihydro-1H,5H-pyrazolo[1,2-a]pyrazol-1-one, an addition salt thereof or a solvate thereof.

Among the compounds of formula (II) it will be preferred to use 2-[(3-aminopyrazolo[1,5-a]pyrid-2-yl)oxy]ethanol, an addition salt thereof or a solvate thereof.

For the vast majority, the 3-aminopyrazolo[1,5-a]pyridines of formulae (II) and (III) are known compounds and are described especially in patent U.S. Pat. No. 5,457,200. These compounds may be prepared according to synthetic methods that are well known in the literature and as described, for example, in patent U.S. Pat. No. 5,457,200.

As examples of derivatives of formula (III), mention may be made of the following compounds:

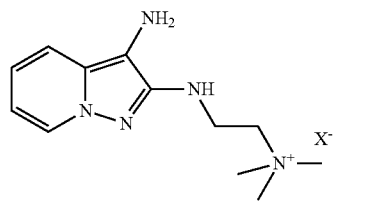

[2-(3-Amino-pyrazolo[1,5-a]pyridin-2-ylamino)-ethyl]-trimethyl-ammonium salt

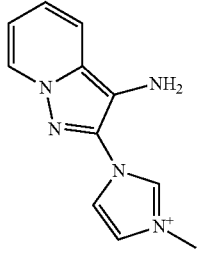

3-(3-Amino-pyrazolo[1,5-a]pyridin-2-yl)-1-methyl-3H-imidazol-1-ium salt

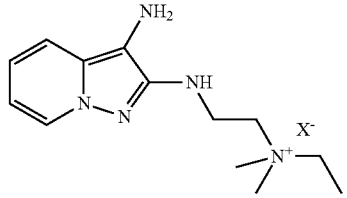

[2-(3-Amino-pyrazolo[1,5-a]pyridin-2-ylamino)-ethyl]-ethyl-dimethyl-ammonium salt

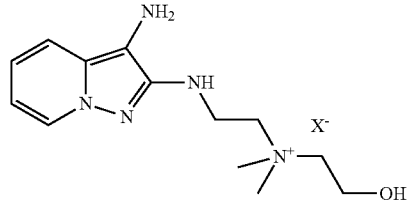

[2-(3-Amino-pyrazolo[1,5-a]pyridin-2-ylamino)-ethyl]-(2-hydroxy-ethyl)-dimethyl-ammonium salt

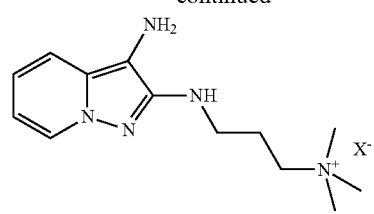

[3-(3-Amino-pyrazolo[1,5-a]pyridin-2-ylamino)-propyl]-
trimethyl-ammonium salt

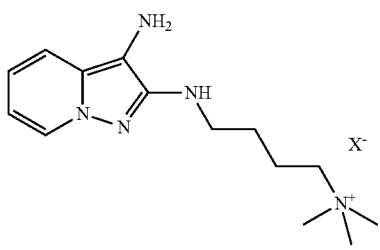

[4-(3-Amino-pyrazolo[1,5-a]pyridin-2-ylamino)-butyl]-
trimethyl-ammonium salt

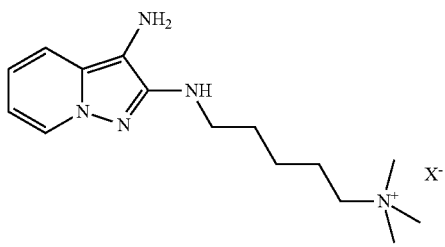

[5-(3-Amino-pyrazolo[1,5-a]pyridin-2-ylamino)-pentyl]-
trimethyl-ammonium salt

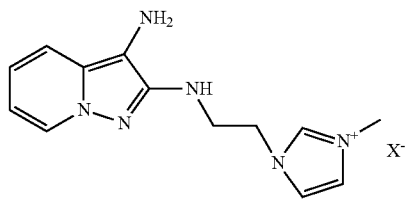

3-[2-(3-Amino-pyrazolo[1,5-a]pyridin-2-ylamino)-ethyl]-
1-methyl-3H-imidazol-1-ium salt

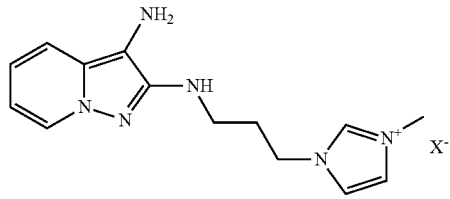

3-[3-(3-Amino-pyrazolo[1,5-a]pyridin-2-ylamino)-propyl]-
1-methyl-3H-imidazol-1-ium salt

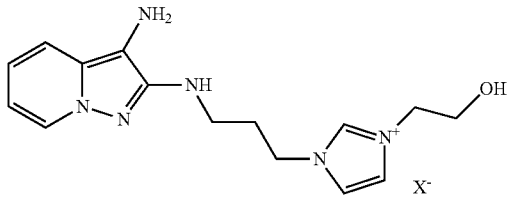

3-[3-(3-Amino-pyrazolo[1,5-a]pyridin-2-ylamino)-propyl]-
1-(2-hydroxy-ethyl)-3H-imidazol-1-ium salt

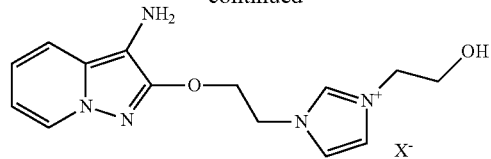

3-[2-(3-Amino-pyrazolo[1,5-a]pyridin-2-yloxy)-ethyl]-
1-(2-hydroxy-ethyl)-3H-imidazol-1-ium salt

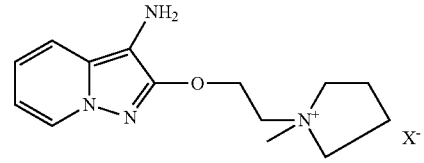

1-{2-[(3-aminopyrazolo[1,5-a]pyridin-2-yl)oxy]ethyl}-
1-methylpyrrolidinium salt

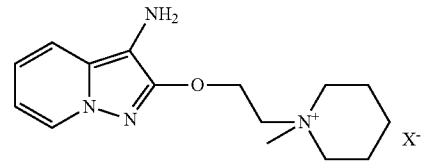

1-{2-[(3-aminopyrazolo[1,5-a]pyridin-2-yl)oxy]ethyl}-
1-methylpiperidinium salt

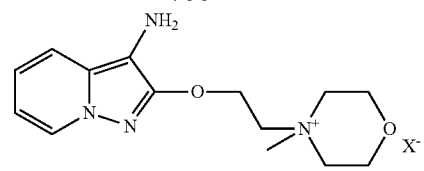

4-{2-[(3-aminopyrazolo[1,5-a]pyridin-2-yl)oxy]ethyl}-
4-methylmorpholin-4-ium salt

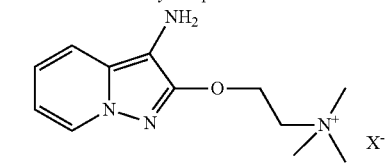

{2-[(3-aminopyrazolo[1,5-a]pyridin-2-yl)oxy]ethyl}-
trimethyl-ammonium salt

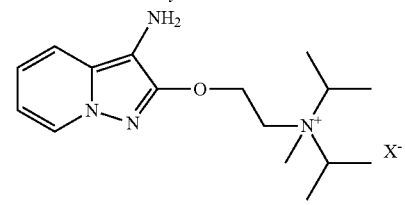

{2-[(3-aminopyrazolo[1,5-a]pyridin-2-yl)oxy]ethyl}-
diisopropyl-methyl-ammonium salt

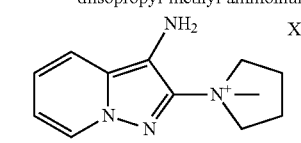

1-(3-aminopyrazolo[1,5-a]pyridin-2-yl)-1-
methylpyrrolidinium salt

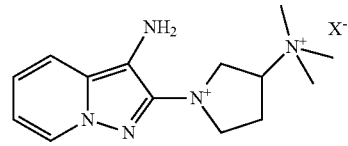

[1-(3-Amino-pyrazolo[1,5-a]pyridin-2-yl)-pyrrolidin-3-yl]
trimethyl-ammonium salt

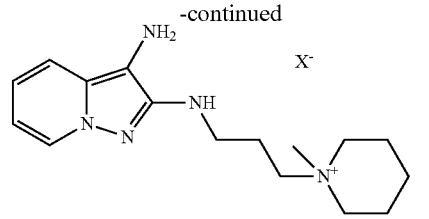

1-[3-(3-Amino-pyrazolo[1,5-a]pyridin-2-ylamino)-propyl]-1-methylpiperidinium salt

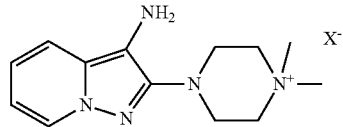

4-(3-Amino-pyrazolo[1,5-a]pyridin-2-yl)-1,1-dimethyl-piperazin-1-ium salt

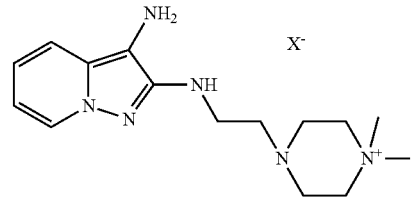

4-[2-(3-Amino-pyrazolo[1,5-a]pyridin-2-ylamino)-ethyl]-1,1-dimethyl-piperazin-1-ium salt

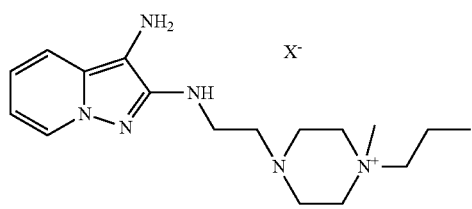

4-[2-(3-Amino-pyrazolo[1,5-a]pyridin-2-ylamino)-ethyl]-1-methyl-1-propyl-piperazin-1-ium salt

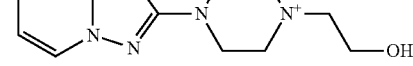

4-(3-Amino-pyrazolo[1,5-a]pyridin-2-yl)-1-(2-hydroxy-ethyl)-piperazin-1-ium salt

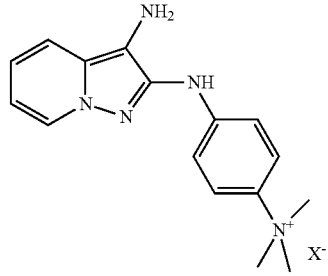

[4-(3-Amino-pyrazolo[1,5-a]pyridin-2-ylamino)-phenyl]-trimethyl-ammonium salt

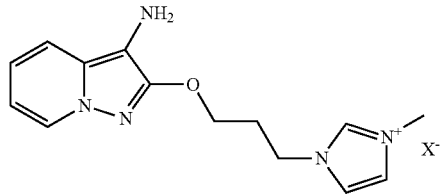

3-[3-(3-Amino-pyrazolo[1,5-a]pyridin-2-yloxy)-propyl]-1-methyl-3H-imidazol-1-ium salt

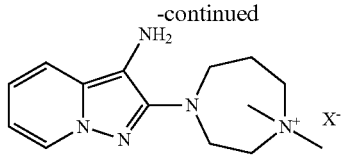

4-(3-Amino-pyrazolo[1,5-a]pyridin-2-yl)-1,1-dimethyl-[1,4]diazepan-1-ium salt

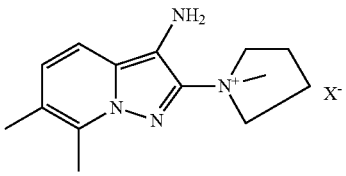

1-(3-amino-6,7-dimethylpyrazolo[1,5-a]pyridin-2-yl)-1 methylpyrrolidinium salt

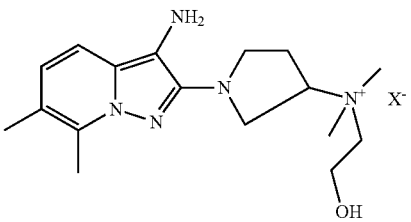

[1-(3-Amino-6,7-dimethyl-pyrazolo[1,5-a]pyridin-2-yl)-pyrrolidin-3-yl]-(2-hydroxy-ethyl)-dimethyl-ammonium salt

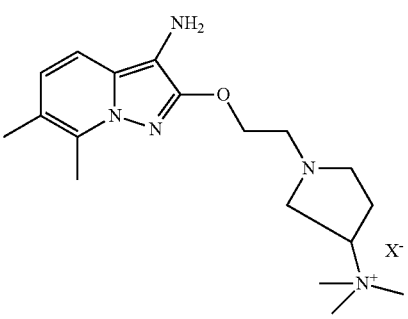

{1-[2-(3-Amino-6,7-dimethyl-pyrazolo[1,5-a]pyridin-2-yloxy)-ethyl]-pyrrolidin-3-yl}-trimethyl-ammonium salt

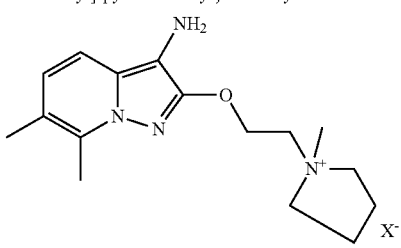

1-{2-[(3-amino-6,7-dimethylpyrazolo[1,5-a]pyridin-2-yl)oxy]ethyl}-1-methylpyrrolidin salt

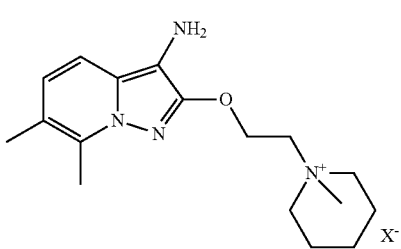

1-{2-[(3-amino-6,7-dimethylpyrazolo[1,5-a]pyridin-2-yl)oxy]ethyl}-1-methylpiperidium salt -continued

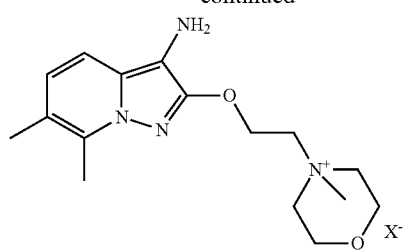

4-{2-[(3-amino-6,7-dimethylpyrazolo[1,5-a]pyridin-2-yl)oxy]ethyl}-4-methylmorpholin-4-ium salt

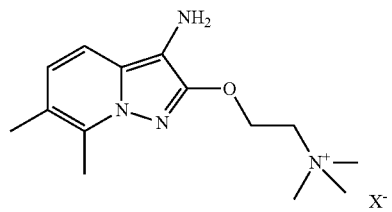

{2-[(3-amino-6,7-dimethylpyrazolo[1,5-a]pyridin-2-yl)oxy]ethyl}-trimethylammonium salt

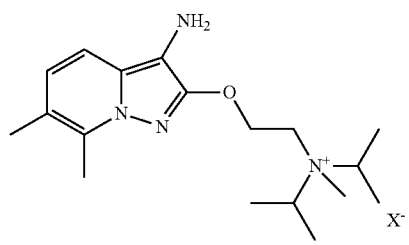

{2-[(3-amino-6,7-dimethylpyrazolo[1,5-a]pyridin-2-yl)oxy]ethyl}-diisopropylmethylammonium salt

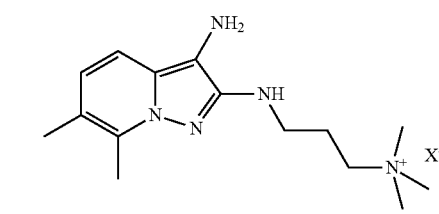

[3-(3-Amino-6,7-dimethyl-pyrazolo[1,5-a]pyridin-2-ylamino)-propyl]-trimethyl-ammonium salt

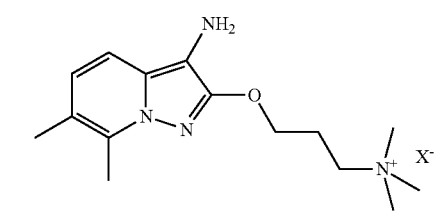

[3-(3-Amino-6,7-dimethyl-pyrazolo[1,5-a]pyridin-2-yloxy)-propyl]-trimethyl-ammonium salt

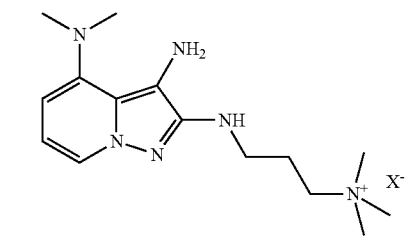

[3-(3-Amino-4-dimethylamino-pyrazolo[1,5-a]pyridin-2-ylamino)-propyl]-trimethyl-ammonium salt -continued

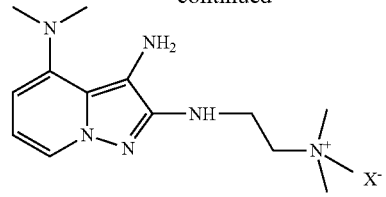

[2-(3-Amino-4-dimethylamino-pyrazolo[1,5-a]pyridin-2-ylamino)-ethyl]-trimethyl-ammonium salt

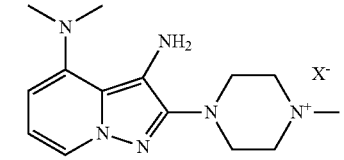

4-(3-Amino-4-dimethylamino-pyrazolo[1,5-a]pyridin-2-yl)-1-methyl-piperazin-1-ium salt

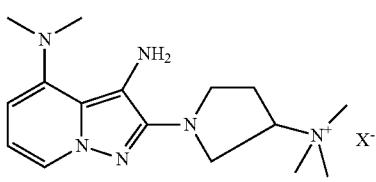

[1-(3-Amino-4-dimethylamino-pyrazolo[1,5-a]pyridin-2-yl)-pyrrolidin-3-yl]-trimethyl-ammonium salt

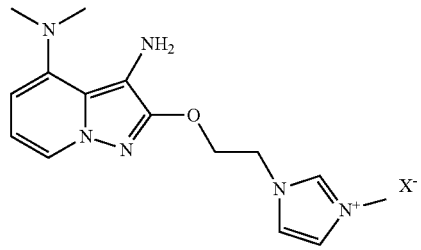

3-[2-(3-Amino-4-dimethylamino-pyrazolo[1,5-a]pyridin-2-yloxy)-ethyl]-1-methyl-3H-imidazol-1-ium salt

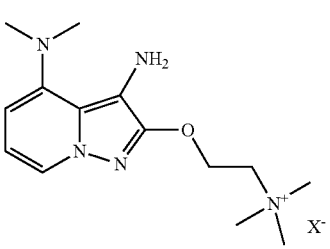

[2-(3-Amino-4-dimethylamino-pyrazolo[1,5-a]pyridin-2-yloxy)-ethyl]-trimethyl-ammonium salt

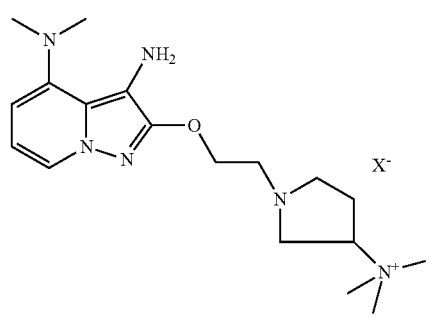

{1-[2-(3-Amino-4-dimethylamino-pyrazolo[1,5-a]pyridin-2-yloxy)-ethyl]-pyrrolidin-3-yl}-trimethyl-ammonium salt The radical X represents an ion or a group of ions for ensuring the electronegativity of the derivative of formula (III).

As heterocyclic bases that are useful for the invention, use will preferentially be made of 2,3-diamino-6,7-dihydro-1H, 5H-pyrazolo[1,2-a]pyrazol-1-one and/or 2-[(3-aminopyrazolo[1,5-a]pyrid-2-yl)oxy]ethanol and/or a salt or solvate thereof, and 2,3-diamino-6,7-dihydro-1H,5H-pyrazolo[1,2-a]pyrazol-1-one and/or a salt or solvate thereof.

As cationic oxidation bases of formula (III), the following bases are most particularly preferred:

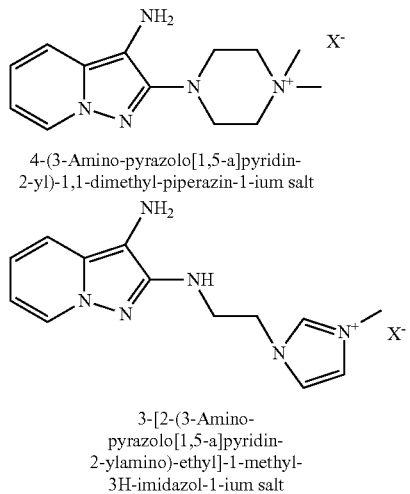

4-(3-Amino-pyrazolo[1,5-a]pyridin-2-yl)-1,1-dimethyl-piperazin-1-ium salt

3-[2-(3-Amino-pyrazolo[1,5-a]pyridin-2-ylamino)-ethyl]-1-methyl-3H-imidazol-1-ium salt The salts of the heterocyclic oxidation bases that may be used according to the invention may be chosen from the hydrochlorides, hydrobromides, sulfates, citrates, succinates, tartrates, lactates, tosylates, methanesulfonates, benzenesulfonates, phosphates and acetates.

The composition of the invention may contain one or more heterocyclic bases described above.

In the composition of the invention, the heterocyclic oxidation base(s) are present in an amount generally between 0.0001% and 20% by weight relative to the total weight of the composition, preferably from 0.005% to 10% by weight and more particularly from 0.01% to 10% by weight relative to the total weight of the composition.

a) 3-(2,5-Diaminophenyl)-1-propanol Oxidation Bases

The composition of the invention comprises c) one or more oxidation bases chosen from 3-(2,5-diaminophenyl)-1-propanol (or 2-γ-hydroxypropyl-para-phenylenediamine) having the following formula, the acid salts thereof or the solvates thereof such as hydrates:

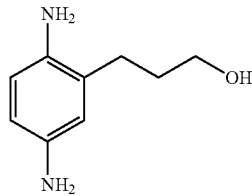

The oxidation base(s) chosen from (2,5-diaminophenyl) propanol, the acid salts thereof or the solvates thereof such as hydrates, according to the invention, may be present in the composition of the invention in an amount ranging from 0.0001% to 20% by weight relative to the total weight of the composition, preferably from 0.005% to 10% by weight and more particularly from 0.01% to 10% by weight relative to the total weight of the composition.

The acid salts that may be used according to the invention may be chosen from hydrochlorides, hydrobromides, sulfates, citrates, succinates, tartrates, lactates, tosylates, benzenesulfonates, phosphates and acetates.

Additional Oxidation Bases

The composition according to the invention may comprise one or more additional oxidation bases other than 3-(2,5-diaminophenyl)-1-propanol and the heterocyclic oxidation bases and the acid salts thereof or the solvates thereof such as hydrates.

As examples of additional benzene-based oxidation bases, mention may be made of para-phenylenediamines other than 3-(2,5-diaminophenyl)-1-propanol, bis(phenyl)alkylenediamines, para-aminophenols, ortho-aminophenols, and the addition salts thereof or solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis((β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl) pyrrolidine, and the addition salts thereof with an acid, or the solvates thereof.

Among the para-phenylenediamines mentioned above, para-phenylenediamine or PPD, para-tolylenediamine or PTD, 2-isopropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, or the solvates thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof, or the solvates thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid, or the solvates thereof.

Among the ortho-aminophenols, examples that may be mentioned include 2-aminophenol, 2-amino-5-methylphenol, 2-amino-6-methylphenol, 5-acetamido-2-aminophenol and the addition salts thereof, or the solvates thereof.

The additional oxidation base(s) according to the invention each advantageously represent from 0.0001% to 10% by weight relative to the total weight of the composition, and preferably from 0.005% to 5% by weight relative to the total weight of the composition.

c) Couplers

The composition of the invention comprises at least one coupler. Among these couplers, mention may be made especially of meta-phenylenediamines, meta-aminophenols, meta-diphenols, naphthalene-based couplers and heterocyclic couplers, and the addition salts or solvates thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2,4-diamino-1-(β-hydroxyethyloxy)benzene, 1-methyl-2-hydroxy-4-β-hydroxyethylamino benzene, 2-methyl-5-aminophenol, 5-amino-6-chloro-2-methylphenol, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid or the solvates thereof, and mixtures thereof.

The coupler(s) each advantageously represent from 0.0001% to 10% by weight relative to the total weight of the composition and preferably from 0.005% to 5% by weight relative to the total weight of the composition of the invention.

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

Additional Dyes

The composition of the invention may also comprise one or more direct dyes. The latter dyes are more particularly chosen from ionic or nonionic species, preferably cationic or nonionic species. These direct dyes may be synthetic or of natural origin. When they are present, the direct dye(s) more particularly represent from 0.0001% to 10% by weight and preferably from 0.005% to 5% by weight relative to the total weight of the composition.

Basifying Agents:

The composition of the invention may also comprise one or more basifying agents. The basifying agent(s) may be mineral or organic or hybrid.

The mineral basifying agent(s) are preferably chosen from ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (T) below:

in which formula (T) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (T) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

Preferably, the basifying agent(s) present in the composition of the invention are chosen from alkanolamines and amino acids in neutral or ionic form, in particular basic amino acids. According to a particularly preferred mode, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first embodiment, the composition predominantly contains ammonia as basifying agent.

According to another embodiment, the composition contains ammonia and at least one other basifying agent, preferably chosen from alkanolamines. In this case, the composition comprises ammonia or a salt thereof, in an amount less than the amount of basifying agent(s) other than ammonia (expressed as $NH_3$). In particular, the composition contains little or no ammonia. Preferably, according to this embodiment, the ammonia content is less than or equal to 0.03% by weight (expressed as $NH_3$), preferably less than or equal to 0.01% by weight, relative to the weight of the composition of the invention. Preferably, the composition contains no ammonia.

Chemical Oxidizing Agent

The composition of the invention may comprise one or more chemical oxidizing agents. The term "chemical oxidizing agent" means an oxidizing agent other than atmospheric oxygen. More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates.

Advantageously, this oxidizing agent is hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Ingredients

The composition according to the invention may also contain various ingredients conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers; anionic, cationic, amphoteric and/or nonionic surfactants.

The above ingredients are generally present in an amount, for each of them, of between 0.01% and 20% by weight, relative to the weight of the composition.

The composition of the invention may be in various forms, for instance a solution, an emulsion (milk or cream) or a gel, preferably in the form of an emulsion.

Processes of the Invention

The composition according to the invention is applied to wet or dry keratin fibres. It is left in place on the fibres for a time generally of from 1 minute to 1 hour and preferably from 5 minutes to 30 minutes. According to a preferred embodiment, the composition applied contains at least one basifying agent and at least one oxidizing agent.

The temperature during the dyeing process is conventionally between room temperature (between 15° C. and 25° C.) and 80° C. and preferably between room temperature and 60° C.

After the treatment, the human keratin fibres are optionally rinsed with water, optionally washed with a shampoo and then rinsed with water, before being dried or left to dry.

According to a preferred embodiment, the composition according to the invention is prepared by mixing at least two compositions, a first composition (A) which comprises the oxidation base 3-(2,5-diaminophenyl)-1-propanol, the heterocyclic base(s) and/or an acid salt or solvate thereof and a second composition (B) which comprises at least one chemical oxidizing agent.

In a preferred variant of this embodiment, at least one of the compositions (A) or (B) comprises the fatty substance(s) as defined previously such that the fatty substance content of the composition resulting from the mixing of compositions (A)+(B) is at least 10%, preferably greater than 25%, preferably greater than 30% by weight, relative to the weight of the composition derived from the mixing of (A)+(B).

According to one embodiment, at least one of the compositions (A) or (B) is aqueous, and preferentially both compositions (A) and (B) are aqueous.

The term "aqueous composition" means a composition comprising at least 5% water. Preferably, an aqueous composition comprises more than 10% by weight of water and more advantageously still more than 20% by weight of water.

In one variant of the invention, at least part of the fatty substance(s) is present in a third composition which is mixed with compositions (A) and (B) under the conditions defined above. Preferably, this third composition is anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as water of crystallization in salts, or traces of water absorbed by the starting materials used in the preparation of the compositions according to the invention.

The examples that follow serve to illustrate the invention without, however, being limiting in nature.

EXAMPLES

Example 1

The following compositions are prepared in which the amounts are expressed in grams of active materials.

| Dye compositions (g %) | | |
| --- | --- | --- |
| Ingredients | Composition A | Composition B |
| Sodium metabisulfite in power form | 0.45 | 0.45 |
| Pure monoethanolamine | 5.1 | 4.93 |
| Ethylenediaminetetraacetic acid | 0.2 | 0.2 |
| 6-Hydroxybenzomorpholine | | 0.16 |
| 1-Methyl-2-hydroxy-4-β-hydroxyethylaminobenzene | 0.22 | |
| 1-β-Hydroxyethyloxy-2,4-diaminobenzene dihydrochloride | | 0.19 |
| 2-Methyl-1,3-dihydroxybenzene (2-methylresorcinol) | 0.3 | 0.05 |
| Purified 5-amino-6-chloro-o-cresol | 0.2 | 0.03 |
| 2,3-Diamino-6,7-dihydro-1H,5H-pyrazolo[1,2-A]pyrazol-1-one dimethane sulfonate | 1.2 | |
| 2-[(3-Aminopyrazolo[1,5-a]pyridin-2-yl)oxy]ethanol hydrochloride | 0.1 | |
| 3-(2,5-Diaminophenyl)propan-1-ol hydrochloride | 0.2 | 0.57 |
| 4-(3-Aminopyrazolo[1,5-a]pyridin-2-yl)-1,1-dimethylpiperazin-1-ium, HCl | | 0.01 |
| Mineral oil (INCI name) | 60 | 60 |
| Perfume | 0.72 | 0.72 |
| Cationic hydroxyethylcellulose (Polyquaternium-67) marketed under the name Softcat Polymer SL-100 by Dow Chemical | 0.19 | 0.19 |
| Deionized water | qs 100 | qs 100 |
| Oxyethylenated stearyl alcohol (2 OE) | 1.13 | 1.13 |
| Oxyethylenated stearyl alcohol (20 OE) | 3.88 | 3.88 |
| Caprylyl/capryl glucoside (alkyl (C8/C10 50/50) polyglucoside (2) in 60% buffered aqueous solution) | 2.4 | 2.4 |
| Oxyethylenated sorbitan monolaurate (4 OE) | 2.4 | 2.4 |
| Vitamin C: ascorbic acid | 0.25 | 0.25 |

| Oxidizing composition C (g %) | |
| --- | --- |
| Ingredients | Composition C |
| Pentasodium pentetate | 0.06 |
| Hydrogen peroxide | 6 |
| Sodium stannate | 0.04 |
| Phosphoric acid | qs pH = 2.2 |
| Tetrasodium pyrophosphate | 0.03 |
| Mineral oil | 20 |
| Hexadimethrine chloride | 0.15 |
| Polyquaternium-6 | 0.2 |
| Water | qs 100 |
| Glycerol | 0.5 |
| Cetearyl alcohol | 6 |
| Steareth-20 | 5 |
| PEG-4 Rapeseedamide | 1.2 |
| Tocopherol | 0.1 |

At the time of use, each of the compositions A and B is mixed with one time its own weight of oxidizing composition C.

The mixtures thus obtained are applied to natural hair containing 90% white hairs.

After a leave-on time of 35 minutes at room temperature, the hair is rinsed and washed with a standard shampoo.

After drying, an attractive Coppery Red Dark Blonde shade of hair is obtained with formula A and a Dark natural shade of hair is obtained with formula B.

Example 3

The following compositions have been prepared in which the amounts are expressed in grams of active materials.

| | C (inv) | C' (comp) |
| --- | --- | --- |
| Ethanolamine | 4 | 4 |
| Sodium LAURYL ETHER SULFATE (2.2 EO) in an aqueous solution (70%) | 2.5 | 2.5 |
| HYDROXYETHYL CELLULOSE (PM: 1.300.000) | 2.5 | 2.5 |
| ANTI-OXYDANT | 0.5 | 0.5 |
| 1-METHYL-2-HYDROXY-4-BETA-HYDROXYETHYLAMINOBENZENE | 0.5 | 0.5 |
| 1-METHYL-2-HYDROXY-4-AMINO-BENZENE | 0.5 | 0.5 |
| 1,3-DIHYDROXYBENZENE (RESORCINOL) | 0.2 | 0.2 |
| 2,3-DIAMINO-6,7-DIHYDRO-1H,5H-PYRAZOLO[1,2-A]PYRAZOL-1-ONE DIMETHANESULFONATE | $4.04 \cdot 10^{-3}$ mol | $4.04 \cdot 10^{-3}$ mol |

-continued

| | | |
|---|---|---|
| 3-(2,5-DIAMINOPHENYL)PROPAN-1-OL-HYDROCHLORIDE | $3.43 \times 10^{-3}$ mol | — |
| (2,5-diaminophenyl)ethanol | — | $3.43 \times 10^{-3}$ mol |
| SEQUESTRANT | 2 | 2 |
| Coco-betaine | 3 ma | 3 ma |
| REDUCTEUR (Sodium meta bisulphite) | 0.5 | 0.5 |
| Mineral Oil | 60 | 60 |
| PEG-40 hydrogenated castor oil | 1 | 1 |
| water | Qsp 100 | Qsp 100 |

| Oxyidizing composition | Ox2 |
|---|---|
| Hydrogen peroxide in an aqueous solution 50% | 6 |
| ETIDRONIC Acid, TETRA sodium salt in an aqueous solution (30%) | 0.2 |
| Tetra sodium PYROPHOSPHATE, 10 $H_2O$ | 0.04 |
| SODIUM Salycilate | 0.035 |
| DIMETHYL DIALLYL AMMONIUM CHLORIDE/ACRYLIC ACID COPOLYMERE (80/20) IN AN AQUEOUS SOLUTION (Merquat 280) | 0.74 |
| GLYCEROL | 4 |
| CAPRYLYL/CAPRYL GLUCOSIDE (ALKYL (C8/C10 50/50) POLYGLUCOSIDE IN AN AQUEOUS SOLUTION (60%) | 3 |
| WATER | qsp 100 |

At the time of use, each composition C' and C is mixed with the oxidizing composition O×2 at a weight ratio of 1/1.

The resulting mixture are each applied on natural locks with 90% of white hair (BN) and on permed hair locks with 90% of white hair (BP in an amount of 10 g of the resulting mixture per 1 g of hair, and left for 35 minutes at room temperature (25° C.).

Then the hair was rinsed with water, washed with the "Pro Classics concentrated" shampoo (L'Oréal Professionnel), diluted at 10%, and dried.

Selectivity Evaluation

The color of the hair was determined using the CIE L*a*b* system with a Minolta CM2006D spectrophotometer (illuminant D65, angle 10°, specular component included) in the CIELab system.

According to this system, L* indicates the lightness of the color of the hair.

The chromaticity coordinates are expressed by the parameters a* and b*, a* indicating the axis of red/green shades and b* the axis of yellow/blue shades.

The selectivity of the dyeing is measured by calculating the variation of ΔE according to the formula:

$$\Delta E = \sqrt{(L^* - L_o^*)^2 + (a^* - a_o^*)^2 + (b^* - b_o^*)^2}$$

In which L, a* and b* represent the values measured on permed hair and L0*, a0* and b0* represent the values measured on natural hair.

The selectivity is represented by the difference of color between the colored natural hair representative of the hair roots and permed hair representative of hair tips: the more is the ΔE value, the more the difference of color between natural and permed hair is important. A lesser selectivity is representative of an homogeneity of the coloration between the roots and the tips along the lock of hair.

The following results are obtained:

| | Hair type | L* | a* | b* | ΔE |
|---|---|---|---|---|---|
| C + O2 (inv) | BN | 26.9 | 15.2 | 10.6 | 9.3 |
| | BP | 20.9 | 10.6 | 5.0 | |

-continued

| | Hair type | L* | a* | b* | ΔE |
|---|---|---|---|---|---|
| C' + O2 (comp) | BN | 29.6 | 18.4 | 13.7 | 12 |
| | BP | 21.8 | 12.8 | 6.5 | |

The resulting composition C+O2 according to the invention exhibits a ΔE value lesser than the one obtained with the C'+O2 comparative mixture. The hair coloration resulting from the use of C+O2 provides on hair an improved homogeny coloration along the hair fibers.

The invention claimed is:

1. A composition comprising:
   a) at least one oxidation base chosen from 3-(2,5-diaminophenyl)-1-propanol, acid salts thereof, or solvates thereof;
   b) at least one heterocyclic oxidation base chosen from oxidation bases of pyridine, pyrazolone of formula (I), addition salts thereof, or solvates thereof:

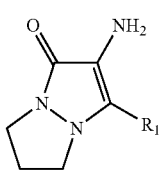

(I)

wherein:
$R_1$ is chosen from an amino group, a $C_1$ to $C_4$ alkyl group optionally substituted with at least one hydroxyl or amino group, or a $C_1$ to $C_4$ alkoxy group optionally substituted with at least one hydroxyl or amino group;
   c) at least one coupler chosen from meta-phenylenediamines, meta-aminophenols, meta-diphenols, naphthalene-based couplers, heterocylic couplers, or the addition salts thereof;
   d) at least one fatty substance, wherein the total amount of fatty substance is more than 30% by weight, relative to the total weight of the composition;
   e) optionally at least one basifying agent; and
   f) optionally at least one chemical oxidizing agent.

2. The composition of claim 1, wherein the at least one fatty substance is chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides and plant waxes, non-silicone waxes, or silicones.

3. The composition of claim 1, wherein the at least one fatty substance is liquid at room temperature and at atmospheric pressure.

4. The composition of claim 1, wherein the at least one fatty substance is chosen from $C_6$-$C_{16}$ hydrocarbons, hydrocarbons containing more than 16 carbon atoms, triglycerides, fatty alcohols, esters of fatty acids, esters of fatty alcohols other than triglycerides, or mixtures thereof.

5. The composition of claim 1, wherein the at least one fatty substance is chosen from liquid petroleum jelly, polydecenes, liquid fatty alcohols, liquid esters of fatty acids, liquid esters of fatty alcohols, or mixtures thereof.

6. The composition of claim 1, wherein the at least one heterocyclic base is an oxidation base of formula (I) chosen from 2,3-diamino-6,7-dihydro-1H,5H-pyrazolo[1,2-a]pyrazol-1-one, addition salts thereof, or solvates thereof.

7. The composition of claim 1, wherein the at least one heterocyclic oxidation base is chosen from compounds according to formula (II) or (III), addition salts thereof, or solvates thereof:

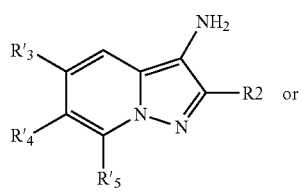

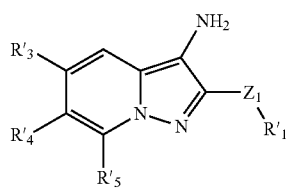

wherein:
R$_2$ is chosen from an amino group, a C$_1$ to C$_4$ alkyl group optionally substituted with at least one hydroxyl or amino group, a C$_1$ to C$_4$ alkoxy group optionally substituted with at least one hydroxyl or amino group; and Z$_1$ is chosen from a covalent bond, a radical —NR'$_6$(CH$_2$)$_q$— or a radical —O(CH$_2$)$_p$—with R'$_6$ representing a hydrogen atom, a C$_1$ -C$_6$ alkyl radical optionally substituted with at least hydroxyl group, wherein p is an integer ranging from 0 to 6, q is an integer ranging from 0 to 6, and R'$_1$ is a cationic radical; further wherein the radicals R'$_3$, R'$_4$, and R'$_5$ are independently chosen from a hydrogen atom or a C$_1$ -C$_4$ alkyl radical which may be substituted, wherein R'$_4$ and R'$_5$ may together form a partially saturated or unsaturated 5- or 8-membered ring.

8. The composition of claim 7, wherein the at least one heterocyclic oxidation base is an oxidation base according to formula (II) wherein R$_2$ is a C$_1$ to C$_4$ alkoxy group optionally substituted with at least one hydroxyl group.

9. The composition of claim 7, wherein the at least one heterocyclic oxidation base is an oxidation base according to formula (II) chosen from 2-[(3-aminopyrazolo[1,5-a]pyrid-2-yl)oxy]ethanol, addition salts thereof, or solvates thereof.

10. The composition of claims 7, wherein the at least one heterocyclic oxidation base is an oxidation base according to formula (III) chosen from 4-(3-aminopyrazolo[1,5-a]pyridin-2-yl)-1,1-dimethylpiperazin-1-ium, addition salts thereof, or solvates thereof.

11. The composition of claim 1, wherein the at least one oxidation base is chosen from 3-(2,5-diaminophenyl)-1-propanol or the acid salts or solvates thereof, and the at least one heterocyclic oxidation base is present in an amount ranging from about 0.0001% to about 20% by weight, relative to the total weight of the composition.

12. The composition of claim 1, comprising at least one basifying agent chosen from ammonia, alkali metal carbonates, alkali metal bicarbonates, sodium hydroxide, potassium hydroxide, organic amines, amino acids, compounds according to formula (T), or mixtures thereof:

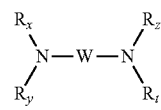

wherein:
W is a divalent C$_1$-C$_6$ alkylene radical optionally substituted with at least one hydroxyl group or a C$_1$-C$_6$ alkyl radical, or optionally interrupted with at least one heteroatom chosen from O or NR$_u$; and R$_x$, R$_y$, R$_z$, R$_t$, and R$_u$, which may be identical or different, are chosen from a hydrogen atom or a C$_1$-C$_6$ alkyl, C$_1$-C$_6$ hydroxyalkyl, or C$_1$-C$_6$ aminoalkyl radical.

13. The composition of claim 1, wherein the at least one basifying agent is chosen from ammonia, alkanolamines, or neutral or ionic amino acids.

14. The composition of claim 1, wherein the at least one chemical oxidizing agent is chosen from hydrogen peroxide.

15. A process for dyeing keratin fibers, comprising:
applying to the keratin fibers a composition comprising:
a) at least one oxidation base chosen from 3-(2,5-diaminophenyl)-1-propanol, acid salts thereof, or solvates thereof;
b) at least one heterocyclic oxidation base chosen from oxidation bases of pyridine, pyrazolone of formula (I), addition salts thereof, or solvates thereof:

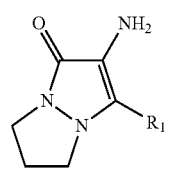

wherein:
R$_1$ is chosen from an amino group, a C$_1$ to C$_4$ alkyl group optionally substituted with at least one hydroxyl or amino group, or a C$_1$ to C$_4$ alkoxy group optionally substituted with at least one hydroxyl or amino group;
c) at least one coupler chosen from meta-phenylenediamines, meta-aminophenols, meta-diphenols, naphthalene-based couplers, heterocyclic couplers, or the addition salts thereof;

d) at least one fatty substance, wherein the total amount of fatty substance is more than 30% by weight, relative to the total weight of the composition;
e) optionally at least one basifying agent; and
f) optionally at least one chemical oxidizing agent.

16. The process of claim 15, wherein the composition is obtained by mixing at least two compositions,
   a first composition (A) comprising the at least one oxidation base and the at least one heterocyclic oxidation base; and
   a second composition (B) comprising the at least one chemical oxidizing agent.

17. The process of claim 16, wherein at least one of the compositions (A) or (B) comprises the at least one fatty substance, wherein the amount of the at least one fatty substance in the composition resulting from the mixing of compositions (A) and (B) is greater than 30% by weight, relative to the weight of the composition derived from the mixing of (A) and (B).

18. The process of claim 16, wherein the composition applied to the fibers comprises a third composition comprising the at least one fatty substance.

19. A multi-compartment device comprising:
   a first compartment containing composition (A) comprising the at least one oxidation base chosen from 3-(2,5-diaminophenyl)-1-propanol, acid salts thereof, or solvates thereof, and at least one heterocyclic oxidation base chosen from oxidation bases of pyridine, pyrazolone of formula (I), addition salts thereof, or solvates thereof:

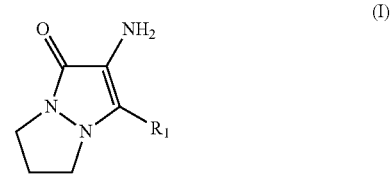

wherein:
$R_1$ is chosen from an amino group, a $C_1$ to $C_4$ alkyl group optionally substituted with at least one hydroxyl or amino group, or a $C_1$ to $C_4$ alkoxy group optionally substituted with at least one hydroxyl or amino group; and a second compartment containing composition (B) comprising at least one
chemical oxidizing agent,
wherein at least one of composition (A) or composition (B) comprises at least one fatty substance, wherein the total amount of fatty substance is more than 30% by weight, relative to the total weight of the composition.

* * * * *